United States Patent
Osika et al.

(10) Patent No.: US 6,960,669 B2
(45) Date of Patent: Nov. 1, 2005

(54) UTILIZATION OF PHOSPHORUS PENTASULFIDE IN THIONYLATIONS USING PHASE TRANSFER CATALYSIS

(75) Inventors: Ewa M. Osika, Cambridge (CA); Walter G. Brouwer, Garrow Hill (GB)

(73) Assignee: Crompton Co./Cie, Elmira (CA)

( * ) Notice: Subject to any disclaimer, the term of this patent is extended or adjusted under 35 U.S.C. 154(b) by 210 days.

(21) Appl. No.: 10/659,411

(22) Filed: Sep. 10, 2003

(65) Prior Publication Data

US 2005/0054860 A1 Mar. 10, 2005

(51) Int. Cl.$^7$ ............................................. C07D 333/56
(52) U.S. Cl. ........................................... 549/57
(58) Field of Search ........................................... 549/57

(56) References Cited

U.S. PATENT DOCUMENTS

| | | | |
|---|---|---|---|
| 5,777,110 A | 7/1998 | Davis et al. | 544/2 |
| 5,965,749 A | 10/1999 | Brouwer | 549/57 |
| 6,372,297 B1 | 4/2002 | Davis et al. | 427/440 |
| 6,555,697 B1 * | 4/2003 | Schlama | 549/471 |

FOREIGN PATENT DOCUMENTS

| | | |
|---|---|---|
| EP | 0715625 | 6/1997 |
| WO | 95/06043 | 3/1995 |

OTHER PUBLICATIONS

Sudalai et al., A Mild and Versatile Catalyst/Reagent for the Preparation of Dithiocarboxylic Esters, Organic Letters, vol. 2, No. 20, pp. 3213–3216, (2000).

Davy et al., One Pot Synthesis of Dithio–esters from Carboxylic Acids, Alcohols, and PS, Chemistry and Industry, p. 824, Dec. 1985.

Rao et al., A PTC Assisted Thionation: Synthesis of 2H–1,4–Benzoxazine–3(4H)–Thiones & 2H–1,4–Benzothiazine–3(4H)–Thiones, Synthetic Communications, 31(22), pp. 3469–3472 (2001).

* cited by examiner

*Primary Examiner*—Deborah C. Lambkin
(74) *Attorney, Agent, or Firm*—Daniel Reitenbach

(57) ABSTRACT

A method is disclosed for the preparation of benzo[b]thiophenecarbodithioic esters of the formula:

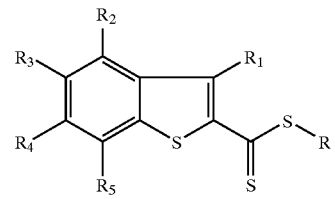

wherein R is alkyl, $R_1$ is hydrogen, halogen, or alkyl, $R_2$, $R_3$, $R_4$, and $R_5$ are independently selected from the group consisting of hydrogen, halogen, alkyl, alkoxy, alkylthio, trifluoromethyl, cyano, and aryl, wherein said method comprises reacting an equivalent of an S-thiol ester of the formula:

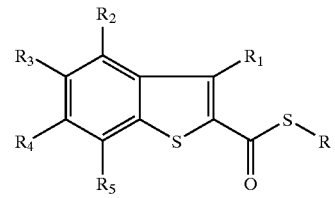

with one-third of an equivalent of $P_2S_5$, 2 equivalents of at least one alkali metal carbonate, about 2.5 mole percent of a phase transfer catalyst, and a catalytic amount of water in hot toluene.

10 Claims, No Drawings

UTILIZATION OF PHOSPHORUS PENTASULFIDE IN THIONYLATIONS USING PHASE TRANSFER CATALYSIS

BACKGROUND OF THE INVENTION

1. Field of the Invention

The present invention relates to the improved utilization of phosphorus pentasulfide in thionylations using phase transfer catalysis. More particularly, the present invention relates to the conversion of S-thiol esters of benzo[b]thiophenecarboxylic acids to the corresponding dithio esters using reduced amounts of phosphorus pentasulfide in the presence of a phase transfer catalyst and catalytic amounts of water. By using less $P_2S_5$, the environmental impact is reduced when the spent $P_2S_5$ is processed for disposal. There is also a positive financial impact when less raw material is used in a chemical process.

2. Description of Related Art

2-Benzo[b]thiophenecarbodithioic esters are important intermediates in the manufacture of material preservation chemicals. See, e.g., EP 0715625.

U.S. Pat. No. 5,965,749 discloses a process for the preparation of a substituted 2-benzo[b]thiophenecarboxylic acid compound or an alkali metal salt thereof, which comprises reacting a halobenzaldehyde derivative with mercaptoacetic acid in the presence of an alkali metal hydroxide and water.

Notwithstanding that esters are not readily converted to their corresponding dithioesters, in U.S. Pat. No. 5,965,749, 2-benzo[b]thiophenecarboxylic acids were first converted to a S-thiolester and subsequently reacted with 1.5 equivalents of $P_2S_5$ in hot toluene to give the corresponding carbodithioic ester. It has been found that it was important that a highly active grade of $P_2S_5$ was necessary in order for the reaction to proceed to completion. Nonetheless, this thionylation required an excessive amount of $P_2S_5$ and consequently, a corresponding amount of spent $P_2S_5$ required particular care in its destruction and subsequent disposal.

It is known that $P_2S_5$ can be used to convert aromatic carboxylic acids in the presence of alkyl thiols to the corresponding dithioesters. Sudalai et al., *Org. Lett.* 2(20):3213–3216, (2000), teaches this conversion using high boiling alkyl thiols and heating the reactants for extended periods of time. This failed to work for 2-benzo[b]thiophenecarboxylic acid.

Davy et al., *Chemistry and Industry*, page 824, December, 1985 teaches a similar conversion to dithiocarboxylic esters, whereby carboxylic acids and $P_2S_5$ in a suitable alcohol in 1,2 dichlorobenzene as solvent were mixed and subsequently heated to 178° C. This method also did not work with 2-benzo[b]thiophenecarboxylic acid.

Rao et al., *Synthetic Communications*, 31(22):3469–3472 (2001) used excess $P_2S_5$, potassium carbonate, and benzyltriethylammonium chloride (TEBA) in dichloroethane to convert a lactam to the corresponding thiolactam. Despite the use of phase transfer catalysts in Rao et al's work, no advantage was expected over that described in thionylations outlined in U.S. Pat. No. 5,965,749.

SUMMARY OF THE INVENTION

The present invention relates to a method for the preparation of 2-benzo[b]thiophene carbodithioic esters of the formula:

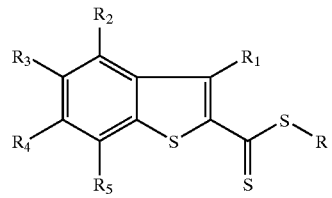

wherein R is alkyl, $R_1$ is hydrogen, halogen, or alkyl, and $R_2$, $R_3$, $R_4$, and $R_5$ are independently selected from the group consisting of hydrogen, halogen, alkyl, alkoxy, alkylthio, trifluoromethyl, cyano, and aryl.

The method comprises reacting the corresponding S-thiol ester of the formula:

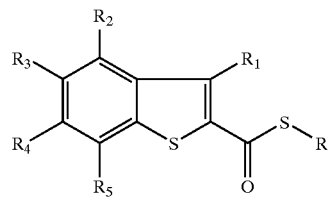

wherein R and $R_1$ thru $R_5$ are as described above, with a preformed complex of 0.33 equivalents of $P_2S_5$ and 2 equivalents of potassium carbonate and then adding about 2.5 mole % of PTC and between 5 and 25 mole % of water. The reaction is conducted in hot toluene. With continued heating, the reaction is monitored for the consumption of all the S-thiol ester, typically in about 7 hours. After cooling to ambient temperature, the spent $P_2S_5$ is removed for separate destruction and disposal. The remaining solution is washed with aqueous sodium bicarbonate solution and water, and, after the removal of the toluene solvent, the dithioester product is isolated in excellent yield and quality.

More particularly, the present invention is directed to a method for the preparation of benzo[b]thiophenecarbodithioic esters of the formula:

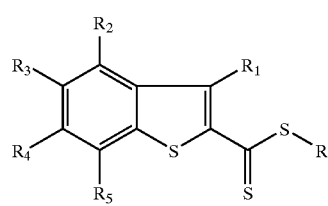

wherein R is alkyl, $R_1$ is hydrogen, halogen, or alkyl, $R_2$, $R_3$, $R_4$, and $R_5$ are independently selected from the group consisting of hydrogen, halogen, alkyl, alkoxy, alkylthio, trifluoromethyl, cyano, and aryl, wherein said method comprises reacting an equivalent of an S-thiol ester of the formula:

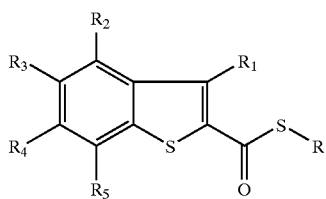

with one-third of an equivalent of $P_2S_5$, 2 equivalents of at least one alkali metal carbonate, about 2.5 mole percent of a phase transfer catalyst, and a catalytic amount of water in hot toluene.

DESCRIPTION OF THE PREFERRED EMBODIMENTS

As disclosed above, The present invention relates to a method for the preparation of 2-benzo[b]thiophene carbodithioic esters of the formula:

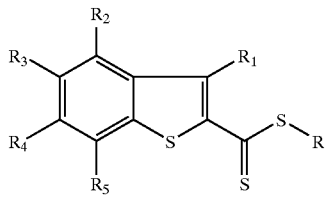

by reacting the corresponding S-thiol ester of the formula:

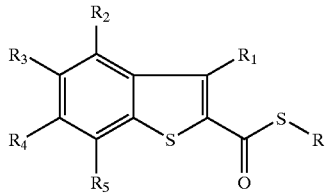

with a preformed complex of 0.33 equivalents of $P_2S_5$ and 2 equivalents of potassium carbonate and then adding about 2.5 mole % of PTC and between 5 and 25 mole % of water, wherein R is alkyl, $R_1$ is hydrogen, halogen, or alkyl, and $R_2$, $R_3$, $R_4$, and $R_5$ are independently selected from the group consisting of hydrogen, halogen, alkyl, alkoxy, alkylthio, trifluoromethyl, cyano, and aryl.

The reaction is conducted in hot toluene. With continued heating, the reaction is monitored for the consumption of all the S-thiol ester, typically in about 7 hours. After cooling to ambient temperature, the spent $P_2S_5$ is removed for separate destruction and disposal. The remaining solution is washed with aqueous sodium bicarbonate solution and water, and, after the removal of the toluene solvent, the dithioester product is isolated in excellent yield and quality.

Where any of R or $R_1$ through $R_5$ are alkyl, they are preferably lower alkyl, more preferably lower alkyl of from 1 to 4 carbon atoms, i.e., methyl, ethyl, n-propyl, isopropyl, n-butyl, isobutyl, sec.-butyl, or tert.-butyl.

Where any of $R_2$ through $R_5$ are alkoxy, they are preferably independently selected from the group consisting of lower alkoxy, more preferably lower alkoxy of from 1 to 4 carbon atoms, i.e., methoxy, ethoxy, n-propoxy, isopropoxy, n-butoxy, isobutoxy, sec.-butoxy, or tert.-butoxy.

Where any of $R_2$ through $R_5$ are alkylthio, they are preferably independently selected from the group consisting of lower alkylthio, more preferably lower alkylthio of from 1 to 4 carbon atoms, i.e., methylthio, ethylthio, n-propylthio, isopropylthio, n-butylthio, isobutylthio, sec.-butylthio, or tert.-butylthio.

Where any of $R_1$ through $R_5$ are halogen, they are preferably independently selected from the group consisting of fluorine, chlorine, bromine, or iodine.

In a preferred embodiment of the present invention, S-ethyl 2-benzo[b]thiophenecarbothioate (EBCT) was reacted with 0.33 equivalents of $P_2S_5$, two equivalents of potassium carbonate, and 2.5 mol % of the TEBA and a catalytic amount of water in hot toluene, thereby producing the corresponding dithioester (EBCD) in excellent yield and quality. This amount of $P_2S_5$ used is greatly reduced from that used by Rao et al in their experiments and also the amount of $P_2S_5$ disclosed in U.S. Pat. No. 5,965,749. An added advantage over Rao et al was that toluene could be used instead of the chlorinated solvent dichloroethane.

This reaction may be represented by the equation:

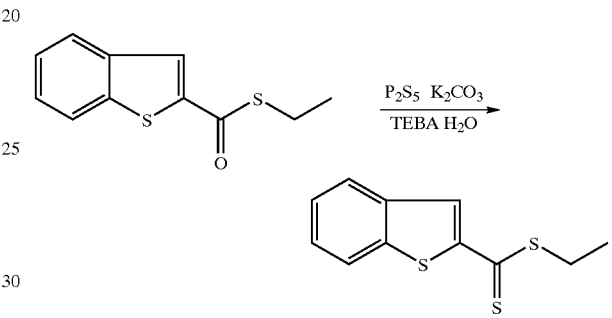

An important consideration in these experiments is that a complex is formed between the $P_2S_5$ and potassium carbonate before the PTC and water are added.

The use of catalytic amounts of water in PTC reactions is well established in solid-liquid reaction mixtures and leads to the formation of a third phase which coats the solid particles. This additional phase, termed the "omega" phase, can contain various species during the course of the reaction. The omega phase provides an alternative lower energy pathway for the transfer of species across phases, see *Phase-Transfer Catalysis* C. M. Starks et. al., Chapman and Hall.

Various features and aspects of the present invention are illustrated further in the examples that follow. While these examples are presented to show one skilled in the art how to operate within the scope of the invention, they are not intended in any way to serve as a limitation upon the scope of the invention.

EXAMPLES

Example 1

Preparation of Ethyl 2-benzo[b]thiophenecarbodithioate

Under nitrogen, a mixture of phosphorus pentasulfide (2.22 grams, 0.01 mol) and potassium carbonate (2.76 grams) in toluene (40 mL) was stirred and refluxed for one hour. After cooling to 70° C., S-ethyl 2-benzo[b]thiophenecarbothioate, (EBCT), (6.11 grams, 0.0275 mol), benzyltriethylammonium chloride, (TEBA), (0.165 gram, $7.2\times10^{-4}$ mol) and water (90 μL) were added and gradually heated to 105° C. An exotherm was observed at around 90–100° C. and the reaction temperature was controlled and finally maintained at 105° C. and held for 2 hours.

Periodically, the reaction was monitored by thin layer chromatography (TLC) using $CH_2Cl_2$:hexane, 40:60 for vanishing EBCT substrate. The reaction was complete after a further one hour. The reaction mixture was cooled to ambient temperature, spent $P_2S_5$ was removed by filtration, the filtrate was washed with toluene, and the combined toluene solutions were washed with aqueous sodium bicarbonate, water, and dried over anhydrous sodium sulfate. After the removal of the drying agent, the toluene was removed to leave a deep red oil that solidified. This solid was identified by its nmr spectrum as ethyl 2-benzo[b]thiophenecarbodithioate, (EBCD), 6.6 grams. The nmr spectrum showed pure material. $^1H$ nmr ($CDCl_3$): δ 8.04 (s, 1H), 7.83 (m, 2H), 7.42 (m, 2H), 3.40 (t, 2H), 2.44 (q, 3H), c.f. spectrum 2837-90-1-EMO. HPLC analysis gave EBCT, 0.45% and EBCD, 100.62%.

Example 2

Under nitrogen, a mixture of potassium carbonate (14.60 grams) and $P_2S_5$ (11.80 grams, 0.053 mol) was stirred and brought to gentle reflux and maintained as such for one hour. The reaction mixture was cooled to 62.1° C. and charged with a mixture of 33.37% EBCT toluene solution (97.30 grams, 89.2%, 0.13 mol), water (0.38 gram) and TEBA (0.80 gram, 3.5 mmol). With stirring, the reaction mixture was gradually heated to reflux. At 98.5° C. a slight exotherm was noted and the reaction was allowed to remain at reflux. TLC ($CH_2Cl_2$:hexane, 40:60) showed that after a post reaction time of 2 hours and 50 minutes the reaction was almost complete. After cooling to ambient temperature, the reaction mixture was filtered, the filtrate was washed with toluene (55 mL) and the combined toluene solutions were washed with 7% aqueous sodium bicarbonate solution (1×25.4 gram and 1×11.3 gram). Removal of the toluene left technical EBCT, 33.34 grams, HPLC analysis gave EBCT, 2% and EBCD, 92.43%.

Example 3

Example 2 was repeated except that water was omitted from the reaction. After a post reaction time of four hours, TLC indicated the reaction was only about 60% complete. The reaction was stopped and the product isolated as in Example 2. HPLC analysis gave EBCT, 28.3% and EBCD, 62.2%.

Example 4

Example 2 was repeated except that water was not added until after one hour and 45 minutes of post reaction time with EBCT. After a further 2 hours of post reaction time with the water, TLC showed the reaction was complete. The product was isolated as in Example 2. HPLC analysis gave EBCT, 0.85% and EBCD, 87.01%.

In view of the many changes and modifications that can be made without departing from principles underlying the invention, reference should be made to the appended claims for an understanding of the scope of the protection afforded the invention.

What is claimed is:

1. A method for the preparation of benzo[b]thiophenecarbodithioic esters of the formula:

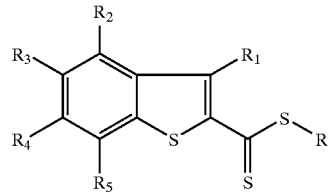

wherein R is alkyl, $R_1$ is hydrogen, halogen, or alkyl, $R_2$, $R_3$, $R_4$, and $R_5$ are independently selected from the group consisting of hydrogen, halogen, alkyl, alkoxy, alkylthio, trifluoromethyl, cyano, and aryl, wherein said method comprises reacting an equivalent of an S-thiol ester of the formula:

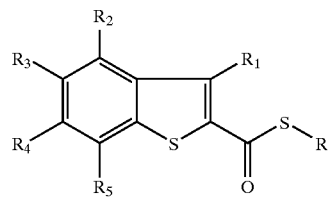

with one-third of an equivalent of $P_2S_5$, 2 equivalents of at least one alkali metal carbonate, about 2.5 mole percent of a phase transfer catalyst, and a catalytic amount of water in hot toluene.

2. The method of claim 1 wherein R is methyl or ethyl and $R_1$ $R_2$, $R_3$, $R_4$, and $R_5$ are independently selected from the group consisting of hydrogen, chlorine, $C_1$–$C_4$ alkyl, and trifluoromethyl.

3. The method of claim 2 wherein $R_1$ $R_2$, $R_3$, $R_4$, and $R_5$ are hydrogen.

4. The method of claim 3 wherein R is ethyl.

5. The method of claim 1 wherein the alkali metal carbonate is potassium carbonate or cesium carbonate.

6. The method of claim 5 wherein the alkali metal carbonate is potassium carbonate.

7. The method of claim 1 wherein the phase transfer catalyst is benzyltriethylammonium chloride or tetrabutylammonium bromide.

8. The method of claim 7 wherein the phase transfer catalyst is benzyltriethylammonium chloride.

9. The method of claim 7 wherein the phase transfer catalyst is tetrabutylammonium bromide.

10. The method of claim 1 wherein R is ethyl, $R_1$, $R_2$, $R_3$, $R_4$, and $R_5$ are hydrogen, the alkali metal carbonate is potassium carbonate, and the phase transfer catalyst is benzyltriethylammonium chloride.

* * * * *